United States Patent [19]

Rensing et al.

[11] Patent Number: 5,527,760
[45] Date of Patent: Jun. 18, 1996

[54] PROCESS FOR THE PROTECTION OF PLANT SEEDS AND APPARATUS TO CARRY OUT SAID PROCESS

[75] Inventors: Cornélis W. Rensing, Oissel; Hubert Sainsard, Louviers, both of France

[73] Assignee: Ciba-Geigy Corporation, Tarrytown, N.Y.

[21] Appl. No.: 410,645

[22] Filed: Mar. 24, 1995

Related U.S. Application Data

[63] Continuation of Ser. No. 182,075, which is a continuation of PCT/EP92/01571, Jul. 11, 1992, published as WO93/01705, abandoned.

[30] Foreign Application Priority Data

Jul. 17, 1991 [FR] France .................... 91 09035

[51] Int. Cl.⁶ .................. A01N 25/16; A01N 25/26; A01C 1/06
[52] U.S. Cl. .................. 504/100; 47/57.6; 71/DIG. 1; 427/4
[58] Field of Search ............... 504/100; 427/4; 514/187; 71/DIG. 1

[56] References Cited

U.S. PATENT DOCUMENTS

| | | | |
|---|---|---|---|
| 3,957,695 | 5/1976 | Davies et al. | 252/532 |
| 4,624,694 | 11/1986 | DelliColli | 71/77 |
| 5,035,814 | 7/1991 | Maaser | 252/8.7 |
| 5,087,475 | 2/1992 | Bazin et al. | 427/4 |

FOREIGN PATENT DOCUMENTS

| | | |
|---|---|---|
| 0010630 | 5/1980 | European Pat. Off. . |
| 0400914 | 12/1990 | European Pat. Off. . |
| 2368890 | 5/1978 | France . |
| 2603154 | 3/1988 | France . |

OTHER PUBLICATIONS

Soviet Inventions Section PQ, Week 8228, Jul. 1982 Derwent Publications Ltd., London, GB.

Onoprienko, N. A. Derwent Abstract of SU865,169. 1981.

Primary Examiner—S. Mark Clardy
Attorney, Agent, or Firm—Edward McC. Roberts

[57] ABSTRACT

An improved process for the phytoprotection of plant seeds, wherein there is simultaneously applied to the seeds, on the one hand, at least one first liquid composition containing at least one phytoprotection product, and on the other hand, a foam formed from a second composition, containing at least one nonphytotoxic foaming agent.

19 Claims, 1 Drawing Sheet

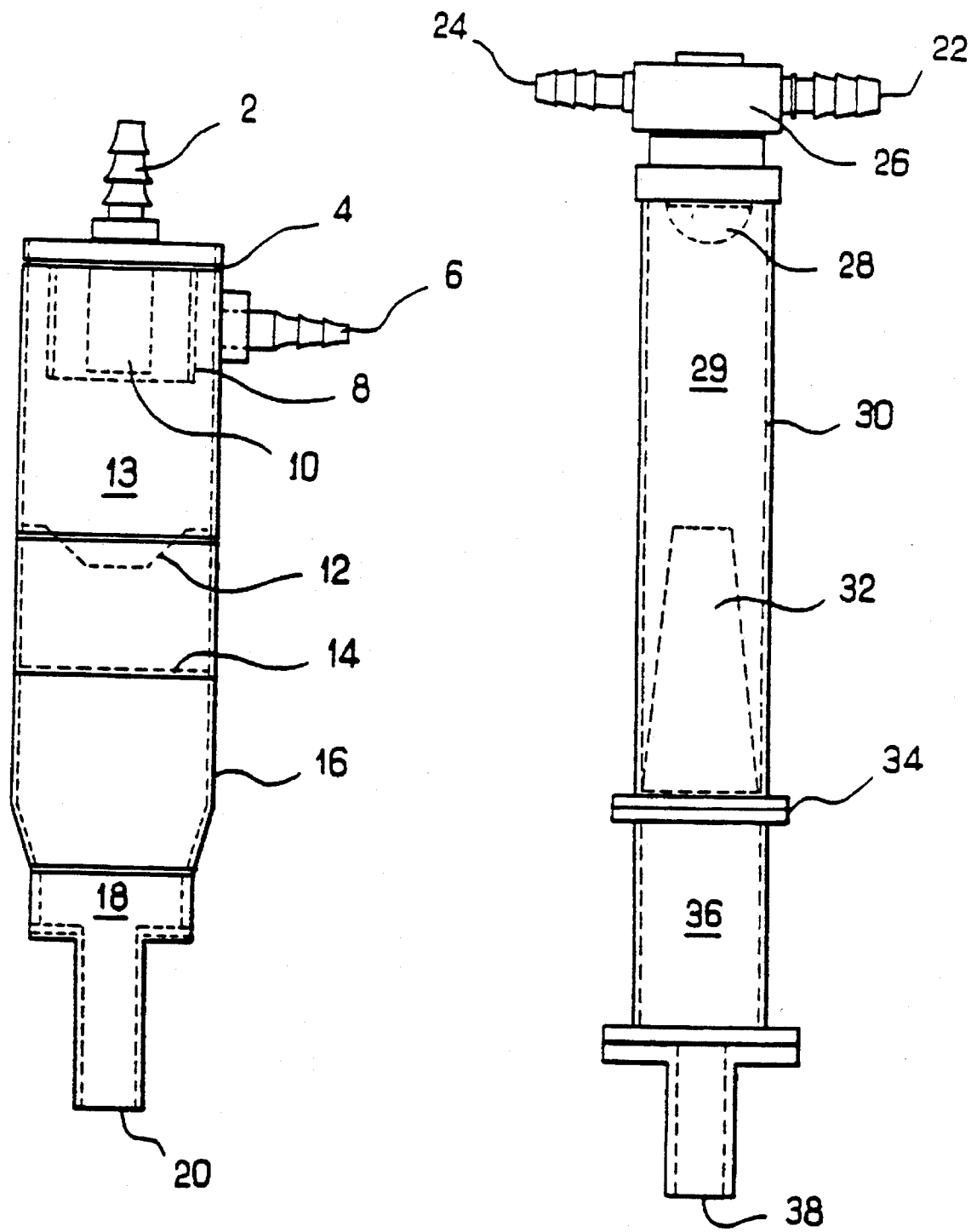
FIG_1   FIG_2

PROCESS FOR THE PROTECTION OF PLANT SEEDS AND APPARATUS TO CARRY OUT SAID PROCESS

This application is a continuation of U.S. patent application Ser. No. 08/182,075, filed Jan. 13, 1994, now abandoned, which is a 371 of PCT/EP92/01571.

It is known that the treatment of seeds leads generally to an increase in the relative moisture level of the seeds. However, seeds are very sensitive to moisture which activates their germination. The tolerance of grain to water varies according to the geographical origin of production and the species of seeds. Therefore since treatment with a phytoprotection product is, for example, carried out in October for February-March sowings, it must not bring about more than 1 to 2% moisture on average in order to avoid any premature start to germination.

Drying of the seeds after treatment may be employed, but this can alter the germinating ability.

Treatment by finely sprayed suspensions in order to form a "mist" does not give satisfactory results because the cloud of droplets has a tendency to move in a body and is deposited on the seeds in a too heterogeneous fashion.

With the development of genetically improved seeds such as hybrid wheats, which are thus more expensive, sowing methods are more and more of the seed-by-seed type and no longer by the hand-sowing method (this classical technique requires, for conventional wheat, 150 to 200 kg/hectare).

It is thus important that all the seeds present in sowing receive the same quantity of treatment product. The homogeneity of the treatment also affects each grain which must be treated in a uniform manner; however, by the conventional processes, certain areas such as the seed furrow are more difficult to reach and escape treatment. The untreated space constitutes a favoured access route for parasites.

Finally, for economic reasons and to protect the environment, one of the aims sought in the improvement of these treatments is a reduction in the quantity of active ingredient used by improving the efficiency.

Hence, the present invention relates to a process for the phytoprotection of plant seeds, wherein there is simultaneously applied to the seeds, on the one hand, at least one first liquid composition containing at least one phytoprotection product, and on the other hand, a foam formed from a second composition, containing at least one nonphytotoxic foaming agent, the two compositions being brought separately into contact with the seeds while mixing for a period of time sufficient to ensure homogeneous and even coating of the said seeds.

The length of time during which the seeds are kept in contact with the treatment compositions will vary as a function of the seed type and the phytoprotection product according to the parameters known to those skilled in the art.

The phytoprotection may be applied to plant seeds and more particularly to those varieties which are of interest as agri-foodstuffs, such as wheat, maize, barley, oil-seed rape, sunflower, beet, rice and soya, as well as vegetable and flower seeds.

The seeds thus treated may optionally be pregerminated.

The plant species are defined, inter alia, by their developed surface area. This surface area can vary, for the same weight, as a function of the volume of the seed. It can vary between 20 $m^2$ and 500 $m^2$ per 100 kg of seeds.

The process according to the invention enables the foam volume to be increased despite the presence of antifoaming agents present in all the speciality chemicals intended for seed treatment (Slurry method). In particular, it makes it possible to retain, at the end of the operation, a quantity of foam which is constant whatever the concentration of antifoaming substance contained in the treatment products and to obtain the same results as if the antifoaming agents present had been deactivated.

The use of foam for this type of seed treatment had not been carried out hitherto. It facilitates improvement of the covering power of the treatment for the same volume of starting liquid.

In fact, to provide a continuous film of 50 micrometers on a surface, it is necessary to employ, with a liquid, a volume of 1 liter per 20 $m^2$ or 25 liters per 500 $m^2$.

The simultaneous formation of foam at the time of phytoprotection treatment makes it possible to increase the entire volume developed by the starting solutions and thus to be able to reduce the quantity of water used. With application in the form of a suspension, 800 ml of solution are used on average to treat 80 $m^2$ of seeds which would not be uniformly covered. With the phytoprotection process according to the method prescribed, the 800 ml will enable 20 to 40 liters of foam to be obtained, permitting a homogeneous and uniform covering of the seeds. In this context the foam has a lathering effect.

The reduction in the quantity of solution to be used by this process results in a lower moisture contribution in relation to the conventional process. The measurement carried out on the seeds before and after treatment by the two compositions, of which one is in the form of foam, shows that their moisture content is virtually unchanged by this treatment.

The drying stage is redundant and it is possible to proceed directly to the bagging stage.

The simultaneous use of a foam and a phytoprotection product will also increase the ability to penetrate into the areas of the seed which are difficult to reach. Indeed, the seeds exhibit surface irregularities which result in variations in interfacial tension, especially at the pericarp, upper scutellum, lower scutellum, hilum and pedicel. Conventional treatment methods do not reach the seed furrow and there can be gaps in the protective coating on the seed.

The use of foam makes it possible to multiply the volume of the solution by 20 to 50 and thus to favour seed/solution contact. The foam makes it possible to increase the wettability of the areas of the seed which are difficult to reach. This process thus leads to uniformity in the treatment of each seed, all the seeds being treated.

This process is characterised in that the phytoprotection product comprises an insecticidal, acaricidal and/or fungicidal and/or nutritive active ingredient, optionally combined with other additives which favour controlled germination and wetting, dispersing, colouring, adhesive and stabilising agents.

It is thus possible to use complex speciality chemicals as phytoprotection products.

Examples of suitable phytoprotection products, available commercially in the form of formulations, are as follows:

| | |
|---|---|
| QUINOLATE + AC FL ® SC | |
| Rate of use: | 200 ml/q cereals |
| Composition: | 100 g/l oxine-copper |
| | 250 g/l anthraquinone |
| QUINOLATE PRO FLO ® SC | |
| Rate of use: | 250 ml/q peas, soya, beans, sunflower |
| Composition: | 120 g/l oxine-copper |
| | 120 g/l carbendazim |
| CORMAISON FL ® SC | |
| Rate of use: | 500 ml/q maize |
| Composition: | 200 g/l anthraquinone |
| | 300 g/l captan |
| CORMAISON TX FL ® SC | |
| Rate of use: | 600 ml/q maize |
| Composition: | 147 g/l anthraquinone |
| | 150 g/l carboxin |
| | 150 gA thiram |
| CORMAISON X ® WS | |
| Rate of use: | 400 g/q maize |
| Composition: | 22% anthraquinone |
| | 22% captan |
| | 22% carboxin |
| QUINOLATE PRO AC FL ® SC | |
| Rate of use: | 250 ml/q peas |
| Composition: | 200 g/l anthraquinone |
| | 120 g/l carbendazim |
| | 120 g/l oxine-copper |
| QUINOLATE PLUS MG SAFLO ® SC | |
| Rate of use: | 400 ml/q cereals |
| Composition: | 250 g/l endosulfan |
| | 100 g/l gamma-HCH |
| | 50 g/l oxine-copper |
| AUSTRAL ® SC | |
| Rate of use: | 500 ml/q cereals |
| Composition: | 100 g/l anthraquinone |
| | 60 g/l oxine-copper |
| | 40 g/l tefluffifin |
| GENOIS ® WS | |
| Rate of use: | 200 g/q cereals |
| Composition: | 25% anthraquinone |
| | 10% oxine-copper |
| | 10% prochloraz |
| STYLOR T320 ® SC | |
| Rate of use: | 500 ml/q maize |
| Composition: | 320 g/l thiram |
| | 210 g/l anthraquinone |
| | 15 g/l flutriafol |
| (The above products are available from LA QUINOLEINE Ltd). | |
| APRON ® (available from the company CEBA-GEIGY Ltd) WS | |
| Rate of use: | 100 to 600 g/q maize, peas, sunflower |
| Composition: | 35% metalaxyl | or other seed treatment products.

In addition to the active ingredients, the speciality chemical compositions may contain:

one or more surface agents comprising a wetting agent and dispersing agent, one or more dyes or pigments, inert ingredient(s), an adhesive agent, antifreeze, thickener comprising an antisedimentation and stabilising agent.

The foaming agent is a nonionic, anionic, cationic or amphoteric surfactant or a mixture of two or more of these.

The foaming agents may be chosen especially from:

Nonionic surfactants

Alkanolamide or alkyloamide e.g. cocamide diethanolamide, lauric acid monoisopropanolamide, ethoxylated myristamide.

Fluorocarbons e.g. ethoxylated polyfluorinated alcohol.

Anionic surfactants

Alkanesulfonate e.g. sodium lauryl sarcosinate.

Alkyl aryl sulfonate e.g. sodium alkylbenzenesulfonate.

Derivatives of (poly)carboxylic acid e.g. ammonium lauryl ether carboxylate.

Olefin sulfonate e.g. sodium alpha olefin sulfonate.

Sarcosinate e.g. ammonium cyclohexyl palmitoyl taurinate.

Succinate e.g. disodium N-octadecyl sulfosuccinamate.

Phosphorus derivatives e.g. phosphoric acid esters and their equivalent salts.

Cationic surfactants: e.g. alkylbenzyltrimethylammonium chloride.

Amphoteric surfactants: e.g. betaine.

The foaming agents must not show toxicity to the seed or the plant.

The foam is formed by simultaneously injecting air or gas under pressure into the composition at the time of application to the seeds.

The gas used can be an inert gas or carbon dioxide. The pressure preferably varies between $1 \times 10^3$ and $5 \times 10^5$ Pascals (Pa).

The compositions which enable the process to be carried out thus consist of a composition containing at least one phytoprotection product, and another composition containing at least one nonphytotoxic foaming agent.

The composition containing the foaming agent can also contain a foam-stabilising agent, preferably the copra diethanolamide.

The composition containing the foaming agent can additionally contain a natural or synthetic resin additive which increases its adhesive power.

Examples of natural resins are:

Alginates—salts and organic derivatives.

Cellulose—hydroxy alkyl-, carboxymethyl- and hydroxypropylethers.

Gums—Carrageenan, Guar, Arabic, Ghatti, Karaya, Tragacanth, Locust Bean, Tamarind, Xanthan.

Agar—Polysaccharide.

Pectins.

Examples of synthetic resins are:

Polyacrylamide, polyglycol, polyethylene oxide, polyvinyl alcohol, polyvinyl acetate, polyvinyl pyrrolidone, starch.

The composition containing the foaming agent can contain a colouring agent or pigment in order to demonstrate and assess correct application of the process over the whole surface area of the seeds.

The mixing of the elements constituting the composition of the foaming agent can be carried out beforehand and stored until it is applied. Its application is carried out simultaneously with the phytoprotection product via the intermediacy of the different apparatuses:

an apparatus which supplies the composition containing at least one phytoprotection product, and a second apparatus which causes foam formation, into which the composition containing at least one foaming agent and the gas, under pressure, are introduced.

In a preferred embodiment, the phytoprotection product is present in a concentration of 50 g to 3 kg (or 50 ml to 3 liters if a liquid composition) per 100 kg of seeds.

Preferably, the nonphytotoxic foaming agent is a surfactant present in a concentration of 0.05 g to 100 g per 100 kg of seeds. Particularly preferred is a concentration of 0.1 to 20 g per 100 kg of seeds.

The present invention also relates to phytoprotection apparatus which enables the process to be carried out, and which consists of a foam formation apparatus comprising a first foam formation chamber equipped with openings which allow a gas and the liquid composition to be admitted and containing, downstream of these openings, at least one sieve, this first chamber continuing into a second chamber for compressing and structuring the foam, which ends in an outlet nozzle for the foam, the foam formation apparatus being coupled to a container equipped with a system for mixing the seeds, the container being additionally equipped with an inlet system for the first composition containing the phytoprotection product, through the intermediacy of a nozzle or of any apparatus which allows the flow and/or spraying of this second composition. The foam thus formed will be applied simultaneously with the phytoprotection speciality chemical, for which it serves as vector.

This foam formation apparatus can be combined with conventional seed treatment apparatus.

In general, seeds will be treated during their passage in a container consisting of a rotating-cylinder type mixer or the like, which enables them to be mixed uniformly. The system operates continuously, the seeds are bagged directly at the mixer outlet, the drying stage is redundant and it is possible to proceed directly to the bagging stage.

The process can also be carried out in the form of a noncontinuous treatment.

In one embodiment, the gas inlet and that of the liquid composition are arranged radially, in opposite directions. The introduction is carried out via the body of separated gas/liquid, dual-inlet nozzles which constitute an atomising system. The apparatus contains a circular, wide-angle spraying nozzle immediately adjoining the introduction connector.

The liquid composition is preferably admitted with a pressure varying between $1 \times 10^3$ and $5 \times 10^5$ Pa, at a flow rate of between 1 and 500 l/h. The gas is at a pressure of between $1 \times 10^3$ and $5 \times 10^5$ Pa.

In another embodiment, the gas inlet and that of the liquid composition are arranged perpendicularly to one another. The liquid arrives with a pressure which can vary between $1 \times 10^3$ and $5 \times 10^5$ Pa and a deflector is placed around the liquid inlet system. The gas liquid mixture passes through an injection nozzle containing a conical chamber and leaves it with a flow rate of between 1 and 500 liters/hour.

The gas and liquid inlets are fitted well upstream of a sieve which is intended to allow foams consisting of very fine bubbles to be obtained.

The apparatus contains a foam formation chamber which contains a sieve whose mesh openings are 250 to 2500 μm in size. The mesh openings may be square, round or eliptical, and the size refers to to the diameter or diagonal, depending on the geometry.

In one embodiment, this sieve is generally flat.

In another embodiment, this sieve is frustoconical and is cup-shaped, opening towards the outlet nozzle.

The foam formation chamber can contain, upstream of the sieve of mesh size 250 to 2500 μm, a first sieve having multiform openings of 3 to 10 mm. In a particular embodiment, this sieve is in the shape of a small dish opening towards the means of introduction.

The chamber for compressing and structuring the foam makes it possible to obtain a foam of thicker consistency.

In one embodiment, the compression chamber is defined by a cylindrical element situated downstream and in the extension of the main casing of the apparatus; this element is fixed by flanges between the casing and an ejection system.

BRIEF DESCRIPTION OF THE DRAWINGS

FIG. 1 represents an embodiment of the foam formation apparatus according to the invention.

FIG. 2 represents another embodiment of the foam formation apparatus according to the invention.

The liquid is admitted under pressure through a tube (2) in a direction perpendicular to that of admission of the air or gas under pressure (6), a joint (4) ensures airtightness. A deflector (8) is interposed between the gas inlet and that of the liquid.

The mixture passes through a full cone nozzle (10) and arrives in the foam formation chamber (13) on a first sieve (12) with multiform openings of 3 to 10 mm and then on a second sieve (14) of mesh size 250 to 2500 μm. The tube (16) has a total length of 220 mm and a diameter of 55 mm.

The mixture then passes into the chamber for compressing and structuring the foam (18) which continues through a foam outlet nozzle (20).

The inlets for liquid (22) and gas or air (24) are arranged along the same axis and terminate in the body of the dual-inlet nozzle (26). After passing through a circular wide-angle spraying nozzle (28), the mixture arrives in the foam formation chamber (29) on a conical sieve (32) of mesh size 250 to 2500 μm and 80 mm in length. The conical tube (30) of diameter 34 mm and of length 250 mm is fixed by flanges (34) to the chamber for compressing and structuring the foam (36). The foam leaves continuously through the outlet nozzle (38).

The angles formed between the axes of the inlets 2 and 6 (FIG. 1) and 24 and 22 (FIG. 2) are 90° and 180° respectively. The apparatus can also be constructed in such a way that the angle between the inlet axes is less than 90°, e.g. 50°, or between 90° and 180°, e.g. 120°.

According to a preferred embodiment of the process, the composition containing a phytoprotection product and water is introduced into the apparatus and the foam obtained with the surfactant is administered simultaneously.

The phytoprotection product is preferably CORMAISON T FL® available from LA QUINOLEINE Ltd.

The foaming agent is preferably ethoxylated polyfluoro alcohol.

The treatment slurry containing the phytoprotection composition is introduced under pressure into a nozzle or with the help of an apparatus for dispersing into droplets.

The foaming agent is introduced under pressure in a nozzle inlet of the applicator represented in FIG. 2.

Compressed air is introduced through the other inlet under a pressure of $1 \times 10^3$ to $5 \times 10^5$ Pa. The apparatus is coupled to a screw-type mixer in which, for example, maize seeds, of the Jaquar variety, are circulating.

The volume of the foam produced by the process is multiplied by a factor of 50 in relation to that of the equivalent liquid. The treatment is carried out by continuous spraying over the passing seeds.

A homogeneous treatment of the surface of the pericarp is observed and the scutellum and the pedicel of the grain are covered, in contrast to the results obtained with a conventional treatment which covers the surface of the grain very unequally. There is virtually no increase in the moisture content.

This confirms well the improvement in the covering and penetrating power of the gas/liquid interfacial treatment, which makes it possible to use a limited quantity of liquid. A continuous film is formed around the seeds, without significant water contribution, by virtue of the simultaneous addition of a composition which contains a surfactant with the application of the seed treatment slurry used in the conventional fashion. The retention of phytoprotection products on the treated seeds is increased. The relative pesticidal power of an active ingredient is thus found to be increased.

Many variants, not essentially different in the quantities and qualities used, may be readily envisaged and are thus contained within the scope of the present invention.

Many adaptations are possible depending on the output required. From preliminary industrial trials it was found that the dimensions of the applicator must be adapted to the required hourly output.

The examples below illustrate the advantages of the phytoprotection process in accordance with the invention applied to wheat and maize, sunflower and pea seeds.

EXAMPLE 1

Wheat species Variety: Fidel

Quantity treated: 25 kg—application by spraying

Mixer: 150 liter cement mixer

Slurry preparation for 100 kg of seeds.

| Conventional method (1) | |
|---|---|
| QUINOLATE + AC FL ® | 250 ml |
| Water | 500 ml |
| Method according to the invention (2) | |
| Phytoprotection composition by spraying | |
| QUINOLATE + AC FL ® | 250 ml |
| Water | 250 ml |
| Foaming agent composition: | |
| sodium salt of alpha $C_{14}$–$C_{16}$ olefin sulfate | 0.1 to 10 g |
| copra diethanolamide | 0.1 to 5 g |
| water | 250 ml |
| compressed air | |
| applicator 1 | |
| Total volume obtained: | |
| According to Method 1 | 750 ml |
| According to Method 2 | 5000–10,000 ml |

Microscopic observations:

Conventional Method (1)

Surface heterogeneously treated,

Noncontinuous film,

Negligible impact in the furrow of the seed.

Method accordign to the invention (2)

Surface uniformly treated,

Continuous film,

Seed furrow 90% covered.

Moisture content of the grains:

Before treatment: 15.5%

After treatment: (1) 16.1% (2) 16[{]jf44b

EXAMPLE 2

Wheat Species Variety: Fidel

| Conventional method (1) by flowing | |
|---|---|
| QUINOLATE + AC FL ® | 250 ml |
| Water | 500 ml |
| Method according to the invention (2) | |
| Phytoprotection composition (by flowing) | |
| QUINOLATE + AC FL ® | 250 ml |
| Water | 250 ml |
| Foaming agent composition: | |
| Na salt of alpha | 0.1 to 20 g |
| $C_{14}$–$C_{16}$ olefin sulfate | |
| Water | 250 ml |
| Cochineal red | 25 g |
| Compressed air | |
| Applicator No. 1 | |
| Total volume obtained: | |
| Method 1 | 750 ml |
| Method 2 | 4000 to 8000 ml |

Microscopic observations of the treated grains:

Conventional method (1)

Surface heterogeneously treated,

Impacts,

Very few impacts in the furrow.

Method according to the invention (2)

Surface uniformly treated,

Continuous film,

Furrow 90% covered.

Moisture content of the grains:

Before treatment: 15.2%

After treatment: (1) 15.7% (2) 15.9%

The quantities of products indicated are expressed in grams or milliliters per 100 kg of seeds.

EXAMPLE 3

Maize Species Variety: Jaguar (toothed half-flat)

Quantity treated: 1000 kg—application by flow

Mixer: screw-type, length 180 cm.

Slurry preparation per 100 kg of seeds.

| Conventional method (1) | |
|---|---|
| CORMAISON T FL ® | 500 ml |
| Water | 500 ml |
| Method according to the invention (2) | |
| Phytoprotection composition | |
| CORMAISON T FL ® | 500 ml |
| Water | 250 ml |
| Foaming agent composition | |
| Ethoxylated polyfluoro alcohol | 0.1–10 g |
| Copra diethanolamide | 0.15 g |
| Water | 250 ml |
| Applicator No. 2 | |
| Compressed air | |
| Volumes obtained: | |
| Method 1: | 1000 ml |
| Method 2: | 8000 to 10,000 ml |

Microscopic observations:

Conventional method (1)

Surface heterogeneously treated,

Noncontinuous film,

Few impacts on the cornet and the hilum.

Method according to the invention (2)

Continuous film,

Corner uniformly treated,

Hilum uniformly treated.

Moisture content of the grains:

Before treatment: 13%

After treatment: (1) 13.8% (2) 13.9[{]jf44b

EXAMPLE 4

Maize species Variety: Jaguar (toothed half-flat)

Quantity treated: 2000 kg—application by continuous spraying on the passing grains.

Mixer: screw-type, length 180 cm.

Slurry preparation per 100 kg of seeds.

| Conventional method (1): | |
|---|---|
| Cormaison T FL ® | 500 ml |
| Water | 500 ml |
| Volume obtained | 1000 ml |
| Method according to the invention (2): | |
| Phytoprotection composition | |
| Cormaison T FL ® | 500 ml |
| Water | 250 ml |
| Foaming agent composition | |
| Ethoxylated polyfluoro alcohol | 0.2 to 20 g |
| Cochineal red | 25 g |
| Polyethylene glycol M 6000 | 50 g |
| Water | 250 ml |
| Applicator No. 2 | |
| Compressed air | |
| Volumes obtained | |
| Method 1 | 1000 ml |
| Method 2 | 12,000 to 15,000 ml |

Microscopic observations:

Conventional method (1):

Surface heterogeneously treated,

Many impacts on the pericarp only,

Few impacts on the scutellum.

Method according to the invention (2):

Surface of the pericarp homogenously treated,

Scutellum and pedicel covered.

Moisture content:

Before treatment: 13%

After treatment: (1) 13.7% (2) 13.9%

The quantities of product indicated are expressed in grams or milliliters per 100 kg of seeds.

CORMAISON T FL®

| Composition based on | 266 g/l thiram |
|---|---|
| | 175 g/l anthraquinone |

EXAMPLE 5

In order to verify the homogeneity of the treatment according to the process of the present invention, a batch of seeds of wheat of the Fidel variety may be treated according to the two application methods as described in Example 2.

In order to analyse the quantity of active material (oxine-copper) on each grain, the sampling may be carried out according to the La Croix method until ±100 grains are obtained.

ANALYTICAL METHOD

Atomic absorption of the copper using a SPECTRA AA 10 spectrometer.

Extraction: Ultrasound—acidified water (HCl)
Number of grains analysed: Conventional method (1): 98
Method according to the invention (2): 101

TABLE 1

Result expressed as a percentage of the theoretical treatment.

| Treatment in relation to the theory | Number of grains | |
|---|---|---|
| 100% | Method 1 | Method 2 |
| <70% | 21 | 0 |
| 70% to 90% | 33 | 6 |
| 90% to 100% | 30 | 86 |
| 110% to 130% | 10 | 8 |
| >130% | 4 | 1 |
| TOTAL | 98 | 101 |

EXAMPLE 6

Verification of the absence of phytotoxicity in the foaming agents used.

Germination trials are carried out on seeds treated respectively as described in Examples 2 and 4. The vigour of the seed is recorded through an index ranging from 1 to 5 (5 being the highest index).

Method: folded filter paper

Temperature: 20° C.±0.5° C.

Reading: 8 days after sowing

Moisture content: 95%

Repetitions: 4×100 grains

TABLE 2

Result on wheat seeds, Fidel variety, treated according to Example 2.

| | AVERAGE OF THE 4 REPETITIONS | | | | | |
|---|---|---|---|---|---|---|
| | | | | LC* % | | |
| | Vigour | Deaths % | Abnormal % | <2 cm | >2 cm | >7 cm |
| Conventional method (1) | 5 | 1.25 | 2.25 | 0 | 1 | 95.5 |
| Method according to the invention (2) | 5 | 1.75 | 1 | 0.25 | 2 | 95 |

TABLE 3

Result on Jaquar maize seeds treated according to Example 4.

| | AVERAGE OF THE 4 REPETITIONS | | | | | |
|---|---|---|---|---|---|---|
| | | | | LC* % | | |
| | Vigour | Deaths % | Abnormal % | <2 cm | >2 cm | >7 cm |
| Conventional method (1) | 5 | 1 | 1.5 | 0.5 | 8 | 89 |
| Method according to the invention (2) | 5 | 0.5 | 1 | 1 | 7.5 | 90 |

*percentage of grains which, after germination, have a coleoptile length (LC) in the ranges indicated.

EXAMPLE 7

Verification of the moisture content expressed in percentage by weight and analysed according to the Chopin method.

METHODS USED

A—noncontinuous soaking in water containing a phytoprotection product

B—noncontinuous soaking in a foam formed from a mixture of water, foaming agent and the phytoprotection product. Degree of expansion: 20 times C—by continuous or noncontinuous spraying, according to the conventional methods, with water containing a phytoprotection product D—by spraying composition 1 plus composition 2 according to the method described in the invention. Degree of expansion: 20 times.

Table 4 (below) illustrates results expressed as a percentage of water uptake.

TABLE 4

Results expressed as a percentage of water uptake

| | | Moisture content in % | | | |
|---|---|---|---|---|---|
| | | Wheat (varieties) | | | Barley |
| Method used | | Theseus | Maris Huntsman | Fidel | Barba-rossa |
| | Before Soaking or Spraying | 11.4 | 12.2 | 12.6 | 13.8 |
| A | Soaking 5 sec. | 24.7 | 24.6 | 24.3 | 25.4 |
| | Soaking 10 sec. | 26.6 | 25 | 25.1 | 27.2 |
| | Soaking 20 sec. | 27.2 | 26 | 25.4 | 28.4 |
| B | Soaking 5 sec. | 16.6 | 19.4 | 22 | 19.1 |
| | Soaking 10 sec. | 16.3 | 19.2 | 21.5 | 20.7 |
| | Soaking 20 sec. | 18.4 | 23.5 | 24.2 | 23.9 |
| C | Spraying 1 l* | 12.2 | 13.0 | 13.4 | 14.7 |
| C1 | Spraying 2 l* | 13.1 | 14.1 | 14.4 | 15.6 |
| D | Spraying 1 l* | 12.3 | 13 | 13.4 | 14.7 |
| D1 | Spraying 2 l* | 13.2 | 13.9 | 14.3 | 15.5 |

1 or 2 l per 100 kg of grains, for trials C and D
10 or 20 ml per 1 kg of grains

TABLE 5

Increase in weight

| Trial sample: | 10 kg of grains |
| Soaking time: | 10 sec. |
| Spraying time | |
| per 100 ml: | 10 sec. |
| per 200 ml: | 20 sec. |

Results expressed in kilograms

| | | | | C | | D | |
|---|---|---|---|---|---|---|---|
| | Variety | A | B | 100 ml | 200 ml | 100 ml | 200 ml |
| Wheat | Theseus | 11.52 | 10.49 | 10.08 | 10.19 | 10.08 | 10.18 |
| | Maris Hunts-man | 11.30 | 10.70 | 10.09 | 10.18 | 10.09 | 10.19 |
| | Fidel | 11.25 | 10.69 | 10.09 | 10.19 | 10.09 | 10.18 |
| Barley | Barba-rossa | 11.40 | 10.69 | 10.09 | 10.18 | 10.08 | 10.08 |

We claim:

1. A process for wet-treating seeds with an acaricidal, fungicidal, insecticidal or nutritive agent, which comprises the steps of applying to the seeds at least one liquid composition containing at least one active ingredient selected from the group consisting of an acaricide, a fungicide, an insecticide and a nutritive agent, and a foam formed from a second composition which is an aqueous composition containing at least a nonphytotoxic foaming agent, the liquid composition and the foam being brought separately into contact with the seeds while being mixed for a time sufficient to ensure homogeneous and even coating of the seeds.

2. A process according to claim 1, wherein the liquid composition further contains at least one of an agent which controls germination, a wetting agent, a dispersing agent, a coloring agent, an adhesive and a stabilizing agent.

3. A process according to claim 2, wherein the active ingredient is present in a concentration of 50 g to 3 kg (or 50 ml to 3 l if the active ingredient is a liquid per 100 kg of seeds.

4. A process according to claim 1, wherein the foaming agent is one or more of a nonionic surfactant, an anionic surfactant, a cationic surfactant and an amphoteric surfactant.

5. A process according to claim 1, wherein the foam is formed by injecting air or other gas under pressure into the second composition.

6. A process according to claim 1, wherein the second composition additionally contains a foam-stabilizing agent.

7. A process of claim 6, wherein the foam-stabilizing agent is copra diethanolamide.

8. A process according to claim 1, wherein the second composition additional contains an additive which increases its adhesive power.

9. A process according to claim 1, wherein the nonphytotoxic foaming agent is a surfactant present in a concentration of 0.05 g to 100 g per 100 kg of seeds.

10. A process according to claim 1, wherein the seeds are treated continuously.

11. A process according to claim 1, wherein the seeds are treated noncontinuously.

12. A process according to claim 1, wherein the said foaming agent is a cationic surfactant.

13. A process according to claim 12, wherein the said foaming agent is ethoxylated polyfluorinated alcohol.

14. A process according to claim 1, wherein the foaming agent is a nonionic surfactant.

15. A process of claim 14, wherein the foaming agent is sodium alpha olefin sulfonate.

16. A process according to claim 1, wherein the said foaming agent is a cationic surfactant.

17. A process according to claim 16, wherein the said foaming agent is alkylbenzyltrimethyammonium chloride.

18. A process according to claim 1, wherein the said foaming agent is an amphoteric surfactant.

19. A process according to claim 18, wherein the said foaming agent is betaine.

* * * * *